United States Patent [19]
Carr

[11] 4,170,521
[45] Oct. 9, 1979

[54] PURIFICATION OF TRIAZOLES

[75] Inventor: Richard P. Carr, Cincinnati, Ohio

[73] Assignee: The Sherwin-Williams Company, Cleveland, Ohio

[21] Appl. No.: 907,943

[22] Filed: May 22, 1978

[51] Int. Cl.[2] ............... B01D 3/34; C07D 249/04
[52] U.S. Cl. ..................................... 203/6; 203/38; 203/62; 203/91; 548/257
[58] Field of Search ............... 203/38, 6, 91, 14, 62; 260/308 B

[56] References Cited
U.S. PATENT DOCUMENTS

| | | | |
|---|---|---|---|
| 2,388,499 | 11/1945 | Riethof | 203/38 |
| 2,744,857 | 5/1956 | Kemp | 203/38 |
| 2,861,078 | 11/1958 | Miller | 260/308 B |
| 3,227,726 | 1/1966 | Levy | 260/308 B |
| 3,334,054 | 8/1967 | Howard et al. | 260/308 B |
| 3,564,001 | 2/1971 | Long | 260/308 B |

Primary Examiner—Wilbur L. Bascomb, Jr.
Attorney, Agent, or Firm—John C. Purdue

[57] ABSTRACT

A method for purifying benzotriazole, tolyl-triazole or mixtures of the two is disclosed. The method includes the steps of vacuum distillation of crude triazole and collection of the condensate. The crude triazole contains color bodies, diazotizable impurities which are color body precursors, or both. The color of the distilled triazole is improved by adding to the crude triazole, prior to vacuum distillation, an amount of formaldehyde sufficient for reaction with an appreciable proportion of the color bodies, the color body precursors, or both.

4 Claims, 2 Drawing Figures

PURIFICATION OF TRIAZOLES

DEFINITIONS

The abbreviation BT is used herein to refer to benzotriazole

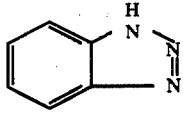

The abbreviation TT is used herein to identify tolyltriazole (isomer mixtures)

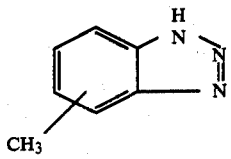

BACKGROUND OF THE INVENTION

BT, TT and mixtures of BT and TT are known compounds which can be produced, for example, by the methods disclosed in U.S. Pat. No. 2,861,078 and by the method disclosed in U.S. Pat. No. 3,227,726. It is sometimes desirable to produce BT, TT, or a mixture of BT and TT having minimum color. To this end, a vacuum distillation is frequently used as a final purification step. It has been found, however, that crude triazoles contain volatile impurities which are color bodies, diazotizable impurities which are color body precursors, or both. Such impurities cannot be removed by vacuum distillation, because they are distilled with the triazole and impart color to the material immediately after distillation or, in the case of color body precursors, cause discoloration after the distilled product stands.

BRIEF DESCRIPTION OF THE PRESENT INVENTION

The present invention is based upon the discovery that the color of BT, of TT, or of a mixture of BT and TT can be improved by addition of a small amount of formaldehyde to the crude product prior to vacuum distillation. The formaldehyde is conveniently added as an aqueous solution because the crude product, having been produced by diazotization, is a wet oil so that the water added with the formaldehyde solution does not further contaminate the material.

It will be appreciated that paraformaldehyde and other formaldehyde polymers could also be used, but that they would form a formaldehyde solution in the water of the wet oil.

It has been found that it is usually desirable to add at least about ½ percent by weight of formaldehyde to the wet oil in order to achieve an appreciable improvement in color. Preferably, at least about ¾ and most desirably at least about 1 percent by weight of formaldehyde is used. There is no upper limit on the amount of formaldehyde that can be employed because any excess that may be present is separated from the triazole product during the vacuum distillation step. As a practical matter, however, it has been found that there may be difficulty in distillation when more than 10 percent by weight of formaldehyde is used and that there is usually no further improvement when amounts of formaldehyde greater than about 5 percent by weight are added to the wet oil. About 3 percent by weight of formaldehyde usually is sufficient to cause as much color improvement as can be achieved.

DESCRIPTION OF THE PREFERRED EMBODIMENT

The following Examples, which are presented solely for the purpose of further illustrating and disclosing, and not of limiting the invention, constitute the best presently known mode for practicing the same.

EXAMPLE 1

Figure 1:
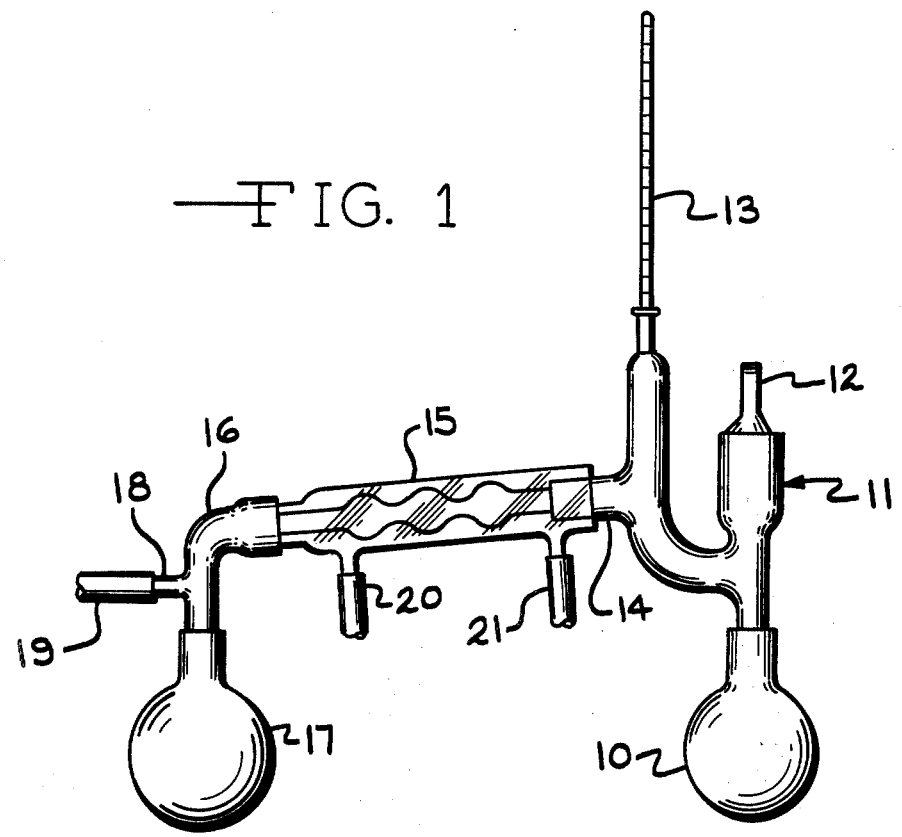
FIG. 1 is a line diagram showing apparatus in which a water stripping stage of a vacuum distillation described in the Examples was carried out.
Figure 2:
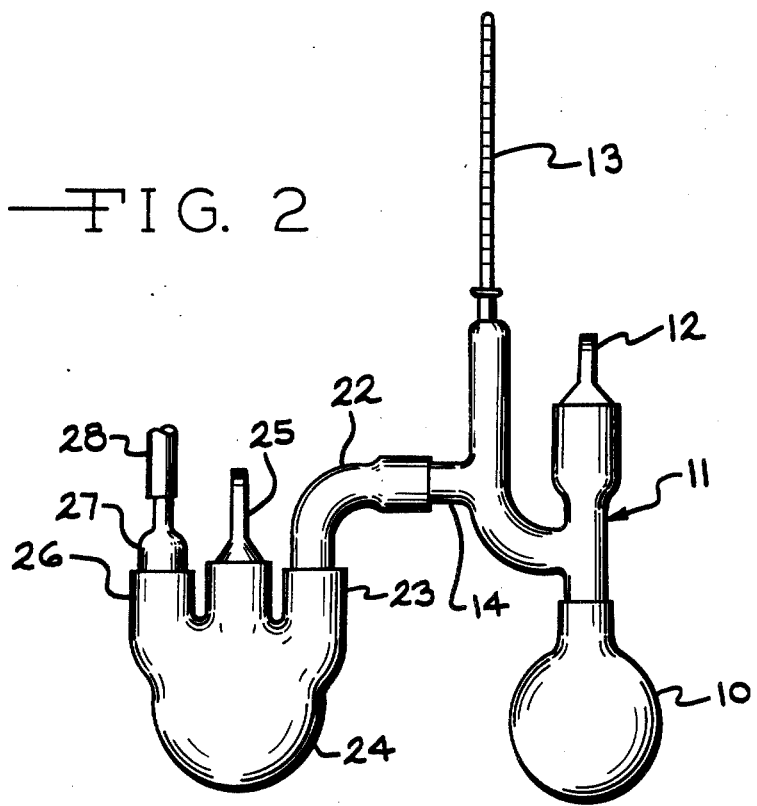
FIG. 2 is a line diagram showing apparatus in which a triazole vacuum distillation was carried out as described in the Examples.

A 500 ml. round-bottom flask 10 (FIG. 1) was charged with 150 g. TT wet oil and 5 g. 37 percent by weight aqueous formaldehyde solution, and filtered with a Claisen head 11. One arm of the Claisen head 11 was closed by a stopper 12, while a second was fitted with a thermometer 13 and a sidearm 14 was engaged with condenser 15. The discharge end of the condenser 15 was connected through an angle 16 to a second round bottom flask 17. The angle 16 had a sidearm which was connected by a line 19 to a vacuum pump (not illustrated). The system was evacuated to an absolute pressure of about 100 mm. Hg, while the contents of the flask 10 were heated by a heating mantle (not illustrated) to cause distillation of water from the wet TT oil in the flask 10. During this distillation tap water at about 20° C. was circulated through the condenser 15, entering through a line 20, and leaving through a line 21; the pressure within the system was gradually reduced to about 20 mm. Hg as the temperature sensed by the thermometer 13 fluctuated between about 50° and 80° C. When the temperature sensed by the thermometer 13 reached 80° C., heating was discontinued temporarily and the condenser 15 was separated from the arm 14 of the Claisen head 11. An angle 22 (FIG. 2) was then attached to the arm 14 and to a neck 23 of a three-neck, round-bottom flask 24. A neck 25 of the flask 24 was stoppered, while a neck 26 received a male tube fitting 27 which was connected through a line 28 to the vacuum pump (not illustrated). The system was then evacuated to an absolute pressure of about 4 mm. Hg, and the flask 10 and contents were heated by a heating mantle (not illustrated) so that the temperature sensed by the thermometer 13 ranged from about 160° to about 180° C. At the end of the distillation, a tarry residue remained in the flask 10, while purified TT had been collected in the flask 24. A 50 percent by weight aqueous solution of the sodium salt of the purified TT had a Gardner color of 8+*, while a solution of 5 g. purified TT in 20 g. polyethylene glycol having a molecular weight of about 200 had a Gardner color of 1+.

*The designation "+" after a Gardner color number means that the solution in question was found to have a color slightly darker than the Gardner designation in question, while the designation "−" means that the color of the solution was slightly less than the Gardner designation in question.

EXAMPLE 2

The flask 10 (FIG. 1) was charged with 150 g. BT wet oil and 5 g. 37 percent by weight aqueous formaldehyde solution. Water was stripped from the wet oil and the BT which remained was distilled, each operation having been carried out substantially as described in Example 1, above. The color of the distilled BT was determined by dissolving a 25 g. sample thereof in sufficient methanol to make 100 ml. solution, separating extraneous material from the solution by filtration, transferring a portion of the filtrate to a 1 cm. curette, and determining the absorbance of the solution at 410 nanometers using a Beckman DU spectrophotometer blanked with reagent grade methanol. The absorbance of the BT distilled as described in Example 2 was found to be 0.04, while that of a similar distilled sample to which no formaldehyde had been added was found to be 0.11.

The procedure of Example 2 was repeated, except that a 10 g. portion of 37 percent by weight aqueous formaldehyde solution was added to the BT wet oil. The color of the BT, after distillation, was found to be substantially the same as that produced as described in Example 2.

For purposes of comparison, but not in accordance with the present invention, the procedure described in Example 1 was repeated, in one instance to distill only the TT wet oil and, in other instances, to distill the TT wet oil plus another material. In each instance, the color of the distilled TT, when dissolved in the polyethylene glycol was poorer than that achieved in the foregoing Example and in all but one instance the color of a 50 percent solution of the distilled material in aqueous sodium hydroxide was poorer than that achieved in the foregoing Example. The materials used, and the color achieved, are set forth in the following Table:

| Additive | Gardner Color Of A 50 Percent Aqueous Solution Of The Sodium Salt Of The Distilled TT | Gardner Color Of A 20 Percent By Weight Solution Of The Distilled TT In Polyethylene Glycol |
| --- | --- | --- |
| Butyraldehyde | 9+ | 3+ |
| Benzaldehyde | 9+ | 4− |
| Anisaldehyde | 10− | 4− |
| Furfural | 11+ | 5 |
| Acetone | 9+ | 5− |
| Acetophenone | 9+ | 4+ |
| Butyrolactone | 11− | 4+ |
| Acetic Anhydride | 10− | 3− |
| Phthalic Anhydride | 8+ | 4− |
| None | 9+ | 4− |

It will be observed from the foregoing Table that phthalic anhydride was the only additive investigated that showed any indication of an improvement in color, and that the indicated improvement with phthalic anhydride was only for the sodium TT solution. Phthalic anhydride has been found to be undesirable for a reason having nothing to do with color, namely, that it has vapor pressure characteristics sufficiently similar to those of BT and TT that, after vacuum distillation, it is present as an impurity in the final product.

It was once postulated that formaldehyde was effective at improving the color of triazoles because of its ability to react with amines as illustrated by the following equation:

$$R\text{—}NH_2 + HCHO \rightarrow R\text{—}N=CH_2 + H_2O$$

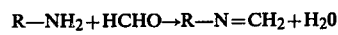

It was further felt that the resulting reaction product had a sufficiently low vapor pressure that it was not distilled with the triazole. The data in the foregoing Table are believed to demonstrate that the stated postulation was incorrect because, otherwise, the materials listed in the Table should also have been effective to improve the color. Accordingly, no theory is suggested as to why formaldehyde, when used as described, is effective at improving the color of triazoles.

It will be appreciated that formaldehyde can be used as described above to improve the color of other triazoles. However, BT, TT and mixtures of the two, from the economic standpoint, are the most significant materials because of availability and cost of diamine materials from which they can be produced.

What I claim is:

1. In a method for purifying a crude benzotriazole, tolytriazole or a mixture of the two, which method includes the steps of vacuum distilling the crude triazole, whereby a triazole vaporizes as distillate, condensing the distillate, and collecting the resultant condensate, and wherein the crude triazole contains color bodies, diazotizable impurities which are color body precursors or both, the improvement comprising subjecting such crude triazole to vacuum distillation in the presence of an amount of formaldehyde sufficient to react with an appreciable proportion of the color bodies, the color body precursors, or both.

2. In a method as claimed in claim 1 the improvement wherein the amount of formaldehyde present is from ½ percent to 10 percent by weight of the crude triazole charged for purification.

3. In a method as claimed in claim 1 the improvement wherein the amount of formaldehyde present is from ¾ percent to 5 percent by weight of the crude triazole charged for purification.

4. In a method as claimed in claim 1 the improvement wherein the amount of formaldehyde present is from 1 percent to 3 percent by weight of the crude triazole charged for purification.

* * * * *